(12) United States Patent
Dooley et al.

(10) Patent No.: US 7,198,680 B1
(45) Date of Patent: Apr. 3, 2007

(54) PROCESS FOR CLEANING SURFACES OF MEDICAL EQUIPMENT

(75) Inventors: Joseph B. Dooley, Kingston, TN (US); Jeffrey G. Hubrig, Knoxville, TN (US); Richard H. DeVault, Portage, MI (US); Rodney D. Parker, Three Rivers, MI (US); John M. Izenbaard, Vicksburg, MI (US)

(73) Assignee: Innovation Services, Inc., Knoxville, TN (US)

( * ) Notice: Subject to any disclaimer, the term of this patent is extended or adjusted under 35 U.S.C. 154(b) by 0 days.

(21) Appl. No.: 11/460,094

(22) Filed: Jul. 26, 2006

(51) Int. Cl.
  *B08B 3/04* (2006.01)
(52) U.S. Cl. .................. 134/26; 510/421; 510/424; 510/425; 134/2; 134/4; 134/28; 134/29; 134/36; 134/41; 134/42
(58) Field of Classification Search ............... 510/421, 510/424, 425; 134/26, 28, 29, 2, 4, 36, 41, 134/42
  See application file for complete search history.

(56) References Cited

U.S. PATENT DOCUMENTS

| | | | |
|---|---|---|---|
| 4,311,618 A * | 1/1982 | Schafer-Burkhard | 510/161 |
| 5,008,030 A * | 4/1991 | Cook et al. | 510/384 |
| 5,348,678 A | 9/1994 | Hodam, Jr. et al. | |
| 5,395,541 A | 3/1995 | Carpenter et al. | |
| 5,731,275 A | 3/1998 | Prevost et al. | |
| 6,326,340 B1 | 12/2001 | Labib et al. | |
| 6,475,434 B1 | 11/2002 | Darouiche | |
| 6,573,230 B1 | 6/2003 | Mertens et al. | |
| 6,730,294 B1 | 5/2004 | Kritzler | |
| 6,762,160 B2 | 7/2004 | Barbeau et al. | |
| 6,846,793 B1 | 1/2005 | Griese | |
| 6,855,678 B2 | 2/2005 | Whiteley | |
| 2004/0048760 A1 * | 3/2004 | Rabon et al. | 510/161 |
| 2004/0209790 A1 * | 10/2004 | Sava et al. | 510/161 |
| 2006/0094780 A1 * | 5/2006 | Rickards et al. | 514/546 |

FOREIGN PATENT DOCUMENTS

| | | |
|---|---|---|
| EP | 774504 | 5/1997 |
| WO | 2004020561 | 5/2004 |
| WO | 2005012472 | 2/2005 |
| WO | 2005123147 | 12/2005 |
| WO | 2006000756 | 1/2006 |

* cited by examiner

*Primary Examiner*—Sharidan Carrillo
(74) *Attorney, Agent, or Firm*—Luedeka, Neely & Graham P.C.

(57) ABSTRACT

A method for cleaning contaminated surfaces of surgical waste management equipment. The method includes rinsing surfaces of the equipment with water to remove water soluble contaminants and waste material. A rinse solution is applied to the surfaces of the equipment to provide a residual film thereon. The rinse solution includes a first nonionic nonylphenol surfactant having an HLB value ranging from about 10 to about 15, a second nonionic nonylphenol surfactant having an HLB value ranging from about 16 to 20, a bio-film permeation agent, and an aqueous solvent. A total of the first surfactant and the second surfactant in the solution ranges from about 2 to about 20 percent by weight of a total weight of the solution and a ratio of the second surfactant to the first surfactant in the solution ranges from about 2:1 to about 4:1.

20 Claims, No Drawings

PROCESS FOR CLEANING SURFACES OF MEDICAL EQUIPMENT

FIELD OF THE DISCLOSURE

The present disclosure is generally directed toward rinse and soak solutions suitable for improving the cleaning of contaminated surfaces. More particularly, the disclosed embodiments are directed to non-corrosive but highly effective rinse and soak solutions for cleaning applications involving surfaces contaminated with biological materials, such as blood, fat, tissue, bone, fecal materials, and surgical rinse solutions.

BACKGROUND AND SUMMARY

Conventional cleaning products for surgical waste management systems typically include highly corrosive industrial cleaning agents because bio-film growth on surgical waste containers is often impervious to conventional enzymatic cleaning solutions or simple detergent cleaning solutions and compositions. Such highly corrosive cleaning agents rely on strong detergents using both acidic and alkaline components that are often corrosive to metal and non-metal surfaces of the waste management system equipment.

Even with the use of such strong detergents, extensive manual scrubbing of such surfaces may be necessary to dislodge the bio-film adhered to the surfaces. Unfortunately, some areas of the waste management canisters are inaccessible for adequate scrubbing and thus leave behind untreated surfaces.

Furthermore, some of the acidic and alkaline components of the cleaning agents are incompatible with disinfectant cleaning agents and may create hazardous liquid and gaseous byproducts in waste discharge plumbing drains and trap assemblies. Accordingly, what is needed is non-corrosive rinsing and soaking solutions that are effective to penetrate bio-films on waste management system surfaces and mobilize and denature entrained protein, lipid complexes, and bacterial residue for removal from the system surfaces. The rinse and soak solutions should also be relatively environmentally friendly so that disposal of the solutions does not create additional hazards.

With regard to the foregoing needs, the disclosure provides a method for effectively cleaning surgical waste management equipment. The method includes rinsing surfaces of the equipment with water to remove water soluble contaminants and waste material. A rinse solution is then applied to the surfaces of the equipment to provide a residual barrier film thereon. The rinse solution includes a first nonionic nonylphenol surfactant having an HLB value ranging from about 10 to about 15, a second nonionic nonylphenol surfactant having an HLB value ranging from about 16 to 20, optionally, a bio-film permeation agent; and an aqueous solvent. A total amount of the first surfactant and the second surfactant in the solution ranges from about 2 to about 20 percent by weight of a total weight of the solution. The solution also has a ratio of the second surfactant to the first surfactant that ranges from about 2:1 to about 4:1.

An advantage of the compositions and methods described herein is that the compositions are not highly corrosive, and do not rely on the use of enzymatic agents which are highly sensitive to alkaline or acid components used in conventional cleaning solutions and to rinse water temperatures. Furthermore, the compositions provide a residual detergent barrier film that may be effective to prevent odor causing bacteria coupled with protein and lipid complexes from attaching to cleaned surfaces. Conventional cleaning solutions may be effective on either waste protein structures or on waste lipid structures, but may not be effective on both. However, the compositions described in more detail herein may be effective as a cleaning agent for both protein-based and lipid-based structures on a surface. The compositions described herein do not promote the attachment of bacterial, protein, lipid, and/or odorous compounds to the cleaned surfaces. Other advantages may be apparent from the following detailed description.

DETAILED DESCRIPTION OF EXEMPLARY EMBODIMENTS

Soaking and rinsing compositions, as provided herein, include several important components dissolved in a major amount of aqueous carrier fluid. The major components include a mixture of certain nonylphenol surfactants in an aqueous carrier fluid. Optional components of the composition include a permeating agent, one or more of chelating agents, an antifoam agent, and a pH buffering agent. Other optional components may include, biocides, disinfection agents, sterilization agents, and the like. The compositions described herein are particularly suitable for bio-film cleaning applications.

Bio-films are contaminants that attach to surfaces of medical equipment, for example, waste management canisters used in operating rooms. Such films may include lipophilic substances such as fatty organic compounds. Residues from surgical operations include components such as blood, fat, tissue, bone, fecal materials, and surgical rinse solutions having lipophilic components. Such lipophilic substances typically have an affinity for metal and polymeric surfaces and may provide a medium for attachment of protein molecules and bacteria to such surfaces. Once attached to the surface of such equipment, cleaning of the equipment surfaces is extremely difficult and time consuming. However, the compositions described herein may be effective to provide both initial cleaning of contaminated surfaces and the subsequent cleaning of such surfaces by providing a removable, residual, barrier detergent film on the surfaces to block proteinaceous and lipophilic substances from attaching to the equipment surfaces.

The barrier detergent film provided by the compositions described herein may be visibly present on the cleaned surfaces as a semi-translucent milky film. Providing such a film on the surfaces goes against conventional wisdom in that the surfaces do not appear perfectly clean. However, this film or barrier layer is effective to deliver active components to the surface of the equipment making attachment of lipophilic contaminants to the surface much more difficult. As a result, rinsing with plain water may be effective to clean the surfaces after each use. After water rinsing, the surfaces may again be protected by applying a rinse solution as described herein to re-apply the film or barrier layer to the cleaned surfaces.

In other applications, described in more detail below, an initial cleaning of the equipment with a soak solution may be necessary to provide a surface sufficiently clean for application of the barrier film thereto. Since the rinse and soak solutions contain primarily the same ingredients but in different amounts, the following detailed description of components is applicable to both the rinse and soak solutions.

A first component of the solutions is a mixture of nonionic surfactants having a relatively high hydrophilic:lipophilic balance (HLB) value. The "hydrophilic: lipophilic balance", or "HLB" value is used as a measure of the relative affinities of the surfactants for water and lipophilic or "oily" substances respectively and correlates with their effectiveness as emulsifiers. HLB values may be calculated for alcohol ethoxylates since it is one fifth of the weight percent of ethylene oxide based on the total mole weight. Other surfactants may be assigned equivalent values by applying more complicated formulae or by measuring their relative affinity for water and oil. An HLB value of 20 represents a completely water soluble, oil insoluble surfactant, while an HLB value of 0 represents a completely oil soluble, and water insoluble surfactant.

The nonionic surfactants which may be used may be selected from linear and branched alkoxylated alcohols and alkoxylated alkylphenols. The alkoxylated alcohols include ethoxylated, propoxylated, and ethoxylated and propoxylated $C_5$–$C_{20}$ alcohols, with about 1–5 moles of ethylene oxide, or about 1–5 moles of propylene oxide, or 1–5 moles of ethylene oxide and 1–5 moles or propylene oxide, respectively, per mole of alcohol. There are a wide variety of products from numerous manufacturers, such as a linear $C_{12}$–$C_{15}$ alcohol ethoxylate with 3 moles of ethylene oxide ("EO") per mole of alcohol, HLB of 7.8, a linear $C_9$–$C_{11}$ alcohol ethoxylate with 2.5 moles of EO: a $C_{12}$–$C_{14}$ ethoxylated alcohol with 3 moles of EO; a $C_{10}$–$C_{12}$ ethoxylated alcohol with 3 moles of EO; and a $C_{12}$–$C_{15}$ ethoxylated alcohol with 3 moles of EO. Secondary ethoxylated alcohols include a $C_{11}$–$C_{15}$ secondary ethoxylated alcohol, with 3 moles of EO. Branched surfactants include tridecyl ethers, such as a tridecyl ether with 3 moles of EO.

Sparingly soluble nonionic surfactants may also be selected from alkoxylated alkylphenols, such as, an ethoxylated nonylphenol with 4 moles of EO, and an HLB of 8.8, an ethoxylated nonylphenol with an HLB of 10.0, an ethoxylated nonylphenol with an HLB of 9.1.

Other non-ionic surfactants which may be used include: fatty acid monoalkylolamide ethoxylates, fatty amine alkoxylates and fatty acid glyceryl ester ethoxylates. Other non-ionic compounds suitable for inclusion in compositions of the present invention include mixed ethylene oxide propylene oxide block copolymers, low relative molecular mass polyethylene glycols, ethylene glycol monoesters, amine oxides and alkyl polyglycosides, alkyl sugar esters including alkyl sucrose esters and alkyl oligosaccharide ester, alkyl capped polyvinyl alcohol and alkyl capped polyvinyl pyrrolidone.

Of the foregoing nonionic surfactants, a combination of a first ethoxylated nonylphenol surfactant having an HLB value ranging from about 10 to about 15 and a second ethoxylated nonylphenol surfactant having an HLB value ranging from about 16 to about 20, may provide the most suitable barrier film on equipment surfaces. Such combination of surfactants may contain from about 10 to about 50 percent by weight of the first surfactant and from about 50 to about 90 percent by weight of the second surfactant. A particularly suitable surfactant combination may contain a ratio of second surfactant to first surfactant ranging from about 2:1 to about 4:1. The total amount of nonionic surfactant in the compositions described herein may range from about 1 to about 20 percent based on a total weight of the composition and typically ranges from about 5 to about 10 percent based on a total weight of the composition. Concentrates containing the components of the compositions described herein may contain from about 10 to about 20 total weight of the nonionic surfactants.

Without desiring to be bound by theory, it is believed that the first surfactant having the lower HLB value deposits first on the surfaces of the equipment to provide a substantially uniform opaque appearance. Then the second surfactant with the higher HLB value deposits on the first surfactant to provide a barrier layer having a textured alligator skin appearance. Because the surfactant combination is substantially water soluble, the barrier film may be easily released from the equipment surface by a simple water rinse.

The barrier film may also have an affinity for other cleaning, disinfecting, sterilizing, and biocidal agents. For example, a substance that promotes molecular cleavage of the bio-film on the equipment surfaces is typically included in the soak and rinse solutions described herein. Because the substance is effective to penetrate the bio-film to the bio-film/surface interface, the substance is referred to herein as a "permeation agent." Suitable permeation agents may be selected from alkyl ether sulfates. Alkyl ether sulfates that may be used, include but are not limited to, sodium coconut alkyl sulfate, potassium coconut alkyl sulfate, potassium lauryl sulfate, sodium lauryl sulfate, sodium yellow fatty alcohol ether sulfate, tallow fatty alcohol sulfate (25 ethylene oxide), tallow fatty ether sulfate, sodium dodecyl benzene sulfonate, sodium stearyl sulfate, sodium palmityl sulfate, sodium decyl sulfate, sodium myristyl sulfate, sodium dodecyl sulfate, potassium dodecyl benzene sulfonate, potassium stearyl sulfate, potassium palmityl sulfate, potassium decyl sulfate, potassium myristyl sulfate, potassium dodecyl sulfate, and mixtures thereof.

Other examples of permeation agents that may be used are sodium lauryl ether sulfate, ammonium lauryl sulfate, ammonium lauryl ether sulfate, sophorose biosurfactant, sodium lauroyl sarcosinate, triethanolamine lauroyl-L-glutamate, sodium myristyl sarcosinate, potassium laurate, sodium dodecane sulfonates, and sodium lauryl ethoxysulfate.

Without desiring to be bound by theoretical considerations, it is believed that the permeation agent may react with the bio-film layer through absorption and permeation to induce molecular cleavage within the bio-film structure so as to initiate adhesive failure at a boundary layer between the bio-film structure and equipment substrate surface. Once adhesive failure at the boundary layer is induced by the permeation agent, the mixture of surfactants enables carrying away the bio-film from the substrate surfaces into the bulk solution.

A particularly useful permeation agent for the rinse and soak solutions described herein is sodium lauryl sulfate. Sodium lauryl sulfate is often referred to as an anionic surfactant. However, in the compositions described herein, sodium lauryl sulfate has more of a detergent effect. The sodium lauryl sulfate is compatible with the barrier film which may contain an amount of sodium lauryl sulfate effective to promote solubilization and mobilization of protein and lipid structures, thereby preventing adhesion of the bio-film to the equipment surfaces. The amount of permeation agent in the compositions described herein may range from about 2 to about 20 percent by weight based on a total weight of the composition. A typical rinse solution may contain from about 2 to about 5 percent by weight of the permeation agent. A rinse solution concentrate may contain from about 4 to about 10 percent by weight of the permeation agent. A typical soak solution may contain from about 5 to about 15 percent by weight of the permeation agent.

A major component of the rinse and soak solutions described herein is an aqueous solvent, such as water. The compositions described herein typically contain a major amount of the solvent which may be provided by potable water. Solubilizing agents may be included in the solvent to aid in solubilizing the components of the composition. For example, concentrates containing the surfactants and permeation agent may require dispersing or solubilizing agents to provide uniform solution concentrates that may be diluted upon use to provide the soak and rinse solutions. Such solubilizing or dispersing agent may include, but are not limited to, alcohols, glycols, glycerines, and the like. The amount of solubilizing or dispersing agent in the compositions described herein may range from about 2 to about 10 percent by weight based on the total weight of the composition.

As set forth above, the primary solvent is an aqueous solvent, typically, water. However, water such as potable water may contain components that interfere with the effectiveness of the rinse and soak solutions. For example, potable water may be classified as hard water or soft water depending on calcium and magnesium content of the water. The following table indicates the hardness of potable water in terms of calcium carbonate equivalent hardness.

TABLE 1

| Water Hardness Characterization | Hardness Values (calcium carbonate mg/liter) |
| --- | --- |
| Soft water | Below 60 |
| Moderately hard | 61 to 120 |
| Hard | 121 to 180 |
| Very hard | 181 to 300 |
| Extremely hard | 301 and above |

The majority of the potable water in the United States falls in the soft to hard range indicated in the table above with only about 30 percent being very hard to extremely hard. However, hard water is believed to promote bio-film formation on the equipment surfaces which may provide the adhesive effects of the bio-film described above. Calcium and magnesium in the potable water may promote polymerization of proteinaceous components which are insoluble in water and may subsequently attach as bacterial and/or malodorous compounds to the lipid components in the bio-film. Accordingly, an optional component of the compositions described herein is a chelating agent which may be used to form complexes with the calcium and/or magnesium in hard water.

Useful chelating agents are those which have two or more carboxyl groups and which are effective at chelating metal ions, especially hard water ions such as calcium and magnesium. Non-limiting examples of suitable chelating agents include gluconic acid, N-hydroxyethylethylenediamine triacetic acid, diethylenetriamine pentaacetic acid, nitrilotriacetic acid, ethylenediamine tetraacetic acid, N-hydroxyethylaminodiacetic acid, methylglycinediacetic acid, and salts thereof. Mixtures of chelating agents may also be used. The foregoing chelating agents may be provided as a water-soluble salt. Suitable water soluble salts include sodium, ammonium, calcium, potassium, ferric, alkylamine, or hydroxyalkylamine.

One of the most commonly used chelating agents is ethylenediamine tetraacetic acid (EDTA) and its salts. Another chelating agent, which is useful for its performance as a chelator and for its desirable property of being biodegradable, is methylglycine diacetic acid (MGDA) and its salts. Other chelating agents that may be used are, for example but not limited to, hydroxyethyl ethylene diaminetriacetic acid (HEEDTA), propanolamine, polyamino-carboxylic acid, diethylenetriamine pentacetic acid (DTPA) and nitrolotriacetic acid (NTA). An amount of chelating agent in the compositions described herein may range from about 0.05 to about 1.0 percent by weight based on a total weight of the composition and the total hardness of the water used as solvent. Rinse and soak solution concentrates may contain from about 0.05 to about 0.5 percent by weight of the chelating agent.

Other components which may be present in the compositions described herein may include but are not limited to pH adjustment agents, antifoam agents, biocides, bacteriacides, sterilization agents, antifungal agents, germicides, and the like.

The major components of the compositions described herein may promote a pH that is slightly acidic to neutral. However, the compositions may be more effective for the cleaning applications described herein if the compositions are slightly alkaline. According, a pH adjustment agent may be added to the composition to provide a pH in the range of from about 6.5 to about 10.0. A more desirable pH of the compositions described herein may range from about 8.5 to about 9.5.

A suitable pH adjustment agent may be selected from weak bases such as, ammonium hydroxide, 2-aminopropanoic acid, ammonia, magnesium hydroxide, methylamine, ethylamine, dimethylamine, trimethylamine, pyridine, glycine, hydrazine, and the like. Accordingly, compositions as describe herein may include from about 0.01 to about 1.0 percent by weight of the pH adjustment agent based on a total weight of the composition. Rinse and soak solution concentrates may contain from about 0.01 to about 0.5 weight percent of the pH adjustment agent.

Another optional component that may be present in the compositions described herein is an antifoam agent. Suitable antifoam agents include silicone and siloxane polymers. A particularly suitable antifoam agent is a polydimethylsiloxane composition. A minor amount of antifoam agent may be used in the compositions described herein to reduce foaming tendencies of the compositions. Accordingly, the rinse and soak solutions may contain from about 0.005 to about 0.05 percent by weight of the antifoam agent. Rinse concentrates may contain from about 0.015 to about 0.03 percent by weight of the antifoam agent.

Depending on the particular application, the rinse and soak solutions described herein may be modified to include other ingredients for specific applications. For example, biocides, sterilization agents, bacteriacides, antifungal agents, and the like may be included to provide additional functionality. For example, compositions as described herein that may be used to disinfect and sterilize surgical waste management equipment may include metal ion compounds; such as silver and/or copper ions at very low levels. Such optional components may be effectively attached to the barrier film deposited on the surfaces of such instruments and may be removed prior to use by rinsing the instruments in water. Optionally, suitably high levels of the permeation agent in the compositions described herein may be effective as a disinfectant.

A particularly useful application of the rinse and soak solutions described herein is for cleaning waste management system canisters used in operating rooms. Such canisters typically have vertical and horizontal surfaces that have an affinity for the bio-films described above. Such canister surfaces may be made of metal and/or polymeric materials such as acrylics, polypropylene, polyethylene, polystyrene, and the like. After an operation, the canisters are emptied and rinsed with water to remove water soluble materials in the canisters. Next, a rinse solution is sprayed into the canisters to provide a residual barrier film on the surfaces of the canisters. Since the residual barrier film may be readily removed by the next water rinse, the residual barrier film may effectively carry away the bio-film components that adhered to the barrier film. Upon drying between duty use cycles, a residual barrier film layer remains on the surfaces of the canister. The rinse solutions may also be applied to the surfaces of a new canister before using the canisters to provide a protective barrier film on the surfaces that may be removed by the water rinse step.

The foregoing procedure is suitable for canisters that have been previously treated with the soak solutions described herein or new canisters that have been treated with the rinse solution before use. In the case of previously used canisters that do not contain the barrier film as provided herein, a more aggressive pre-treatment of the canisters may be required to remove the bio-film before application of the barrier film using the rinse solution. In such instance, the canister is initially rinsed with water as described above. Next, the soak solution is sprayed onto the surfaces of the canister and allowed to penetrate the bio-film. After about fifteen minutes of contact absorption, the soak solution may have penetrated the bio-film contaminate and initiated adhesive delamination of the bio-film from the canister surfaces. Following the rinsing and draining of the solubilized and mobilized bio-film contaminate, the rinse solution is applied to the surfaces of the canister to provide the protective residual barrier film layer upon drying. Exemplary rinse and soak solutions that may be used according to the disclosure are provided in the following table:

TABLE 2

| Component | Rinse solution (wt. %) | Soak solution (wt. %) |
|---|---|---|
| Non-ionic surfactant (HLB = 13) | 2.182 | 1.643 |
| Non-ionic surfactant (HLB = 18.2) | 6.547 | 4.928 |
| Permeation agent | 3.490 | 10.827 |
| Chelating Agent | 0.385 | 0.363 |
| pH adjustment agent | 0.087 | 0.089 |
| Antifoam agent | 0.014 | 0.015 |
| Water | 87.295 | 82.135 |

It is contemplated, and will be apparent to those skilled in the art from the preceding description that modifications and/or changes may be made in the embodiments of the disclosure. Accordingly, it is expressly intended that the foregoing description is illustrative of exemplary embodiments only, not limiting thereto, and that the true spirit and scope of the present disclosure be determined by reference to the appended claims.

The invention claimed is:

1. A method for cleaning contaminated surfaces of surgical waste management equipment, the method comprising the steps of:
    rinsing surfaces of the equipment with water to remove water soluble contaminants and waste material; and
    applying a rinse solution to the surfaces of the equipment to provide a residual film thereon, wherein the rinse solution comprises:
        a first nonionic nonylphenol surfactant having an HLB value ranging from about 10 to about 15;
        a second nonionic nonylphenol surfactant having an HLB value ranging from about 16 to 20;
        a bio-film permeation agent; and
        an aqueous solvent, wherein a total of the first surfactant and the second surfactant in the rinse solution ranges from about 2 to about 20 percent by weight of a total weight of the rinse solution and a ratio of the second surfactant to the first surfactant in the rinse solution ranges from about 2:1 to about 4:1.

2. The method of claim 1, wherein the bio-film permeation agent comprises a composition selected from the group consisting of sodium lauryl sulfate, sodium lauryl ether sulfate, ammonium lauryl sulfate, ammonium lauryl ether sulfate, sophorose biosurfactant, sodium lauroyl sarcosinate, triethanolamine lauroyl-L-glutamate, sodium myristyl sarcosinate, sodium dodecyl sulfate, potassium laurate, sodium dodecane sulfonates, and sodium lauryl ethoxysulfate.

3. The method of claim 1, wherein the rinse solution further comprises a chelating agent.

4. The method of claim 1, wherein the rinse solution further comprises a chelating agent in an amount ranging from about 0.05 to about 1.0 wt. % of the total weight of the rinse solution.

5. The method of claim 1, wherein the rinse solution has a pH ranging from about 6.5 to about 10.0.

6. The method of claim 1, wherein the rinse solution has a pH ranging from about 8.0 to about 9.5.

7. The method of claim 1, wherein the rinse solution comprises from about 1 to about 5 wt. % of the first nonylphenol surfactant; from about 5 to about 10 wt. % of the second nonylphenol surfactant; and from about 5 to about 20 wt. % of the bio-film permeation agent, based on the total weight of the rinse solution.

8. The method of claim 1, wherein the total of the first surfactant and second surfactant in the rinse solution ranges from about 8 to about 10 percent by weight and the bio-film permeation agent ranges from about 3 to about 5 percent by weight based on the total weight of the rinse solution.

9. The method of claim 3, wherein the chelating agent comprises an alkylenediamine tetraacetate compound.

10. The method of claim 8, further comprising applying a soak solution to the surfaces of the equipment prior to applying the rinse solution to the surfaces to provide an initial cleaning of the surfaces, wherein the soak solution comprises from about 5 to about 8 percent by weight of a total of the first surfactant and second surfactant and from about 10 to about 15 percent by weight of the bio-film permeation agent based on a total weight of the soak solution.

11. A method for treating surfaces of surgical waste management equipment to improve cleaning and decontamination of the equipment, the method comprising the steps of:
    applying a residual barrier film to surfaces of surgical waste management equipment by contacting the surfaces of the equipment with a rinse solution, wherein the rinse solution comprises:
        a first nonionic nonylphenol surfactant having an HLB value ranging from about 10 to about 15;
        a second nonionic nonylphenol surfactant having an HLB value ranging from about 16 to 20;
        a bio-film permeation agent; and
        an aqueous solvent, wherein a total of the first surfactant and the second surfactant in the rinse solution ranges from about 2 to about 20 percent by weight of a total weight of the rinse solution and a ratio of the second surfactant to the first surfactant in the rinse solution ranges from about 2:1 to about 4:1; and
    removing the rinse solution from the equipment after a predetermined period of time.

12. The method of claim 11, wherein the bio-film permeation agent comprises a composition selected from the group consisting of sodium lauryl sulfate, sodium lauryl ether sulfate, ammonium lauryl sulfate, ammonium lauryl ether sulfate, sophorose biosurfactant, sodium lauroyl sarcosinate, triethanolamine lauroyl-L-glutamate, sodium myristyl sarcosinate, sodium dodecyl sulfate, potassium laurate, sodium dodecane sulfonates, and sodium lauryl ethoxysulfate.

13. The method of claim 11, wherein the rinse solution further comprises a chelating agent.

14. The method of claim 11, wherein the rinse solution has a pH ranging from about 6.5 to about 10.0.

15. The method of claim 11, wherein the rinse solution has a pH ranging from about 8.0 to about 9.5.

16. The method of claim 11, wherein the rinse solution comprises from about 1 to about 5 wt. % of the first nonylphenol surfactant; from about 5 to about 10 wt. % of the second nonylphenol surfactant; and from about 5 to about 20 wt. % of the bio-film permeation agent, based on the total weight of the rinse solution.

17. The method of claim 11, wherein the total of the first surfactant and second surfactant in the rinse solution ranges from about 8 to about 10 percent by weight and the bio-film permeation agent ranges from about 3 to about 5 percent by weight based on the total weight of the rinse solution.

18. The method of claim 13, wherein the chelating agent comprises an alkylenediamine tetraacetate compound.

19. The method of claim 13, wherein the chelating agent is present in an amount ranging from about 0.05 to about 1.0 wt. % of the total weight of the rinse solution.

20. The method of claim 17, further comprising applying a soak solution to the surfaces of the equipment prior to applying the residual barrier film to the surfaces to provide an initial cleaning of the surfaces, wherein the soak solution comprises from about 5 to about 8 percent by weight of a total of the first surfactant and second surfactant and from about 10 to about 15 percent by weight of the bio-film permeation agent based on a total weight of the soak solution.

* * * * *